(12) United States Patent
Rezach et al.

(10) Patent No.: US 11,583,322 B2
(45) Date of Patent: Feb. 21, 2023

(54) DUAL-SIDED ROD BENDER

(71) Applicant: Warsaw Orthopedic, Inc., Warsaw, IN (US)

(72) Inventors: William A. Rezach, Covington, TN (US); Amanda D. Tong, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 139 days.

(21) Appl. No.: 17/171,303

(22) Filed: Feb. 9, 2021

(65) Prior Publication Data
US 2022/0249137 A1    Aug. 11, 2022

(51) Int. Cl.
*A61B 17/70* (2006.01)
*A61B 17/88* (2006.01)

(52) U.S. Cl.
CPC ................... *A61B 17/7086* (2013.01)

(58) Field of Classification Search
CPC .. A61B 17/8863; A61B 17/7002–7031; A61B 17/7086; B21D 7/063; B21D 7/066; B21D 7/06; B21D 7/022; B21D 7/024; B21F 1/002
See application file for complete search history.

(56) References Cited

U.S. PATENT DOCUMENTS

| | | | | |
|---|---|---|---|---|
| 880,235 | A | * | 2/1908 | Neller .................... B21D 7/063 140/123 |
| 4,077,249 | A | * | 3/1978 | Schmitter ............. B21D 7/063 72/390.2 |
| 5,490,409 | A | * | 2/1996 | Weber .................... B21D 7/022 72/409.1 |
| 5,819,580 | A | * | 10/1998 | Gauthier ............ A61B 17/8863 72/409.1 |
| 6,006,581 | A | * | 12/1999 | Holmes .................. B21D 7/063 72/409.1 |
| 6,463,780 | B1 | | 10/2002 | Kalanish |
| 6,487,889 | B1 | | 12/2002 | Bates et al. |
| 7,454,939 | B2 | | 11/2008 | Garner et al. |
| 7,488,331 | B2 | | 2/2009 | Abdelgany |
| 8,375,764 | B2 | | 2/2013 | Huang |
| 8,491,601 | B2 | | 7/2013 | Schmuck et al. |
| 8,668,699 | B2 | * | 3/2014 | Thomas ............. A61B 17/8863 606/86 R |
| 8,770,006 | B2 | | 7/2014 | Harper |
| 9,044,285 | B2 | | 6/2015 | Harper |

(Continued)

*Primary Examiner* — Jan Christopher L Merene
*Assistant Examiner* — Anna V. Little
(74) *Attorney, Agent, or Firm* — Fox Rothschild LLP

(57) ABSTRACT

A dual-sided rod bender for contouring a rod is disclosed. The rod bender may include a first handle and a second handle pivotably coupled together and extending in a longitudinal direction, respectively, from a proximal end to a distal end. A first side of the rod bender may include a first roller adjacent the distal end, a second roller adjacent the distal end, and a third roller disposed between the first roller and the second roller. A second side of the rod bender may include a fourth roller adjacent the distal end, a fifth roller adjacent the distal end, and a sixth roller disposed between the fourth roller and the fifth roller. The first side may be configured apply a first mechanical advantage to bend a rod and the second side may be configured to apply a second mechanical advantage to bend a rod.

13 Claims, 11 Drawing Sheets

(56) References Cited

U.S. PATENT DOCUMENTS

| | | |
|---|---|---|
| 9,156,075 B2 | 10/2015 | Houle et al. |
| 9,186,195 B2 | 11/2015 | Petit et al. |
| 9,427,275 B2 | 8/2016 | Knoepfle et al. |
| 9,872,716 B2 | 1/2018 | Cordaro et al. |
| 9,999,460 B2 | 6/2018 | Shazly et al. |
| 10,076,376 B2 | 9/2018 | Bootwala et al. |
| 10,189,069 B1 | 1/2019 | Huang |
| 10,327,828 B2 | 6/2019 | Rinner |
| 10,328,476 B2 | 6/2019 | Keeling |
| 10,610,277 B2 | 4/2020 | Schwab et al. |
| 10,702,323 B2 | 7/2020 | Richards et al. |
| 2006/0150699 A1 | 7/2006 | Garner et al. |
| 2009/0222020 A1* | 9/2009 | Schmuck ............ A61B 17/8863 606/205 |
| 2009/0266137 A1 | 10/2009 | Andren et al. |
| 2010/0268119 A1* | 10/2010 | Morrison ............ A61B 17/8863 600/587 |
| 2012/0047980 A1* | 3/2012 | Harper ................... B21D 7/024 72/199 |
| 2012/0240655 A1* | 9/2012 | Houle ................... B21D 7/063 72/476 |
| 2012/0247173 A1* | 10/2012 | Paris ................... A61B 17/8863 72/458 |
| 2014/0260484 A1* | 9/2014 | Harper ................... B21D 7/024 72/211 |
| 2014/0364860 A1* | 12/2014 | Knoepfle ............ A61B 17/8863 606/101 |
| 2015/0047410 A1* | 2/2015 | Petit ................... A61B 17/8863 72/409.1 |
| 2016/0089195 A1* | 3/2016 | Cordaro ............ A61B 17/7085 606/279 |
| 2017/0042597 A1* | 2/2017 | Rinner ................ A61B 17/8863 |
| 2017/0290615 A1 | 10/2017 | Schwab et al. |
| 2019/0298428 A1* | 10/2019 | Richards ............. A61B 17/7002 |
| 2019/0307497 A1 | 10/2019 | Rinner |
| 2020/0214752 A1 | 7/2020 | Schwab et al. |

* cited by examiner

DUAL-SIDED ROD BENDER

FIELD

The present technology is generally related to a surgical instrument for bending a fixing rod used in a medical surgery.

BACKGROUND

Bone structures may be susceptible to a variety of weaknesses and/or diseases such as fractures, degeneration, dislocation, etc. Medical procedures to correct problems such as dislocation of a patient's vertebrae may be corrected through surgery. In various medical surgeries to correct alignment and/or dislocation of a patient's vertebrae, two adjacent vertebrae may be stabilized by means of an elongated fixing rod linking the two adjacent vertebrae. In some cases, the fixing rod used during surgery may need to be bent and/or contoured for accommodating the specific anatomy of a particular patient.

SUMMARY

The techniques of this disclosure generally relate to rod benders for use in bending a surgical rod for a medical procedure. More particularly, this disclosure generally relates to a dual-sided rod bender having a first side for bending a rod of a first angle or degree and a second side for bending a rod of a second angle or degree, for example. Additionally, the first side and second side may each feature an adjustable roller for bending varying rods having different diameters.

In one aspect, the present disclosure provides for a dual-sided rod bender for contouring a rod having a first side and a second. The rod bender may include a first handle and a second handle pivotably coupled together, and the first handle and second handle may each extend in a longitudinal direction from a proximal end to a distal end, respectively. In various embodiments the first side includes: a first roller coupled to the first handle adjacent the distal end, a second roller coupled to the second handle adjacent the distal end, and a third roller disposed between the first roller and the second roller, for example. In various embodiments the second side includes: a fourth roller coupled to the first handle adjacent the distal end, a fifth roller coupled to the second handle adjacent the distal end, and a sixth roller disposed between the fourth roller and the fifth roller, for example. In various embodiments a first geometry defined by the first, second, and third rollers may be configured to provide a first mechanical advantage for bending a rod and a second geometry defined by the fourth, fifth, and sixth rollers may be configured to provide a second mechanical advantage for bending a rod, for example. In various embodiments, the first mechanical advantage may be greater than the second mechanical advantage, for example.

In another aspect, the present disclosure provides that in various embodiments the third roller of the first side may be coaxially aligned with the sixth roller of the second side, for example.

In another aspect, the present disclosure provides that in various embodiments the first handle and second handle are pivotably coupled by a pin.

In another aspect, the present disclosure provides that in various embodiments the first handle includes a first tab and the second handle includes a second tab and a third tab, the first tab may be positioned between the second tab and the third tab, and the pin extends through the first, second, and third tabs, for example.

In another aspect, the present disclosure provides that in various embodiments the third roller may be coupled to the pin at the first side and the sixth roller may be coupled to the pin at the second side, for example.

In another aspect, the present disclosure provides that in various embodiments the first roller may be disposed adjacent an outer edge of the distal end of the first handle, the second roller may be disposed adjacent an outer edge of the distal end of the second handle, and the third roller may be disposed apart from the first roller and second roller towards the proximal end, for example.

In another aspect, the present disclosure provides that in various embodiments the fourth roller may be disposed adjacent an inner edge of the distal end of the first handle, the fifth roller being disposed adjacent an inner edge of the distal end of the second handle, and the sixth roller may be disposed apart from the first roller and second roller towards the proximal end, for example.

In another aspect, the present disclosure provides that in various embodiments the third roller further includes a first adjustment knob including a first nesting channel having a first width and a second nesting channel having a second width, the first adjustment knob being configured to selectively position either one of the first nesting channel or second nesting channel in a position to nest with a rod, for example.

In another aspect, the present disclosure provides that in various embodiments the sixth roller further includes a second adjustment knob including a third nesting channel having a third width and a fourth nesting channel having a fourth width, the second adjustment knob being configured to selectively position either one of the third nesting channel or fourth nesting channel in a position to nest with a rod, for example.

In another aspect, the present disclosure provides that in various embodiments the first handle has a first longitudinal recess disposed on a medial portion of the first handle and a first distal recess disposed on the distal end of the first handle, and the second handle has a second longitudinal recess disposed on a medial portion of the second handle and a second distal recess disposed on the distal end of the first handle, for example.

In another aspect, the present disclosure provides that in various embodiments the first handle has a first support webbing and the second handle has a second support webbing, for example.

In another aspect, the present disclosure provides that in various embodiments a longitudinal plane extends bisects the dual-sided rod bender by passing through a center of the third roller and a center of the sixth roller, for example.

In another aspect, the present disclosure provides that in various embodiments a first angle measured from an intersection of the longitudinal plane and the center of the third roller to a center of the first roller may be the same as a second angle measured from an intersection of the longitudinal plane and the center of the third roller to a center of the second roller, for example.

In another aspect, the present disclosure provides that in various embodiments a third angle measured from an intersection of the longitudinal plane and the center of the sixth roller to a center of the fourth roller may be the same as a fourth angle measured from an intersection of the longitudinal plane and a center of the sixth roller to a center of the fifth roller, for example.

In another aspect, the present disclosure provides that in various embodiments the first angle and the second angle define a first angular relationship and the third angle and the fourth angle define a second angular relationship, the first angular relationship being greater than the second angular relationship, for example.

In another aspect, the present disclosure provides for a method for contouring a rod for use in a surgical procedure. The method may include the step of providing a dual-sided rod bender having a first side including a first plurality of rollers defining a first geometry and a second side including a second plurality of rollers defining a second geometry, for example. The method may further include the steps of moving a first handle and a second handle of the dual-sided rod bender to an open position, and inserting a rod between the first plurality of rollers, for example. The method may further include the steps of rotating at least one roller of the first plurality of rollers such that a first nesting channel faces the rod, seating the rod in the nesting channel, and applying a first external force to the first handle and second handle, for example.

In another aspect, the present disclosure provides for a method including the step of moving the first handle and second handle towards a closed position by applying the first external force, the first external force being based on a mechanical advantage determined by the first geometry, for example.

In another aspect, the present disclosure provides for a method including the steps of moving the first handle and the second handle of the dual-sided rod bender to the open position, and inserting either of the rod or a different rod between the second plurality of rollers, for example. The method may further include the steps of rotating at least one roller of the second plurality of rollers such that a second nesting channel faces either of the rod or the different rod, seating either of the rod or the different rod in the second nesting channel, and applying a second external force to the first handle and second handle, for example.

In another aspect, the present disclosure provides for a method including the step of moving the first handle and second handle towards the closed position by applying the second external force, the second external force being based on a mechanical advantage determined by the second geometry, for example.

In another aspect, the present disclosure provides for a dual-sided rod bender. The rod bender may include a first handle and a second handle pivotably coupled together by a pin, the pin extending through a first tab of the first handle and a second tab and third tab of the second handle, the first tab being positioned between the second tab and third tab, the first handle and second handle each extending in a longitudinal direction from a proximal end to a distal end and defining a first side and a second side of the dual-sided rod bender, for example. In various embodiments the first side includes: a first roller coupled to the first handle adjacent the distal end, the first roller being disposed adjacent an outer edge of the distal end of the first handle, a second roller coupled to the second handle adjacent the distal end, the second roller being disposed adjacent an outer edge of the distal end of the second handle, and a third roller disposed between the first roller and the second roller, for example. In various embodiments, the third roller may be coaxially aligned with the pin and disposed apart from the first roller and second roller towards the proximal end, for example. In various embodiments, the third roller may include a first adjustment knob and a first nesting channel having a first width and a second nesting channel having a second width, for example. In various embodiments, the first adjustment knob may be configured to selectively position either one of the first nesting channel or second nesting channel in a position to nest with a rod, for example. In various embodiments the second side includes a fourth roller coupled to the first handle adjacent the distal end, and the fourth roller may be disposed adjacent an inner edge of the distal end of the first handle, for example. The second side may also include a fifth roller coupled to the second handle adjacent the distal end, and the fifth roller may be disposed adjacent an inner edge of the distal end of the second handle, for example. The second side may include a sixth roller disposed between the fourth roller and the fifth roller, and the sixth roller may be coaxially aligned with the pin and be disposed apart from the first roller and second roller towards the proximal end, for example. Additionally, the sixth roller may include a second adjustment knob and a third nesting channel having a third width and a fourth nesting channel having a fourth width, and the second adjustment knob being configured to selectively position either one of the third nesting channel or fourth nesting channel in a position to nest with a rod, for example. In various embodiments the third roller of the first side may be coaxially aligned with the sixth roller of the second side, for example. In various embodiments a first geometry defined by the first, second, and third rollers may be configured to provide a first mechanical advantage for bending a rod and a second geometry defined by the fourth, fifth, and sixth rollers may be configured to provide a second mechanical advantage for bending a rod, for example. The first mechanical advantage may be greater than the second mechanical advantage, for example, for example.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
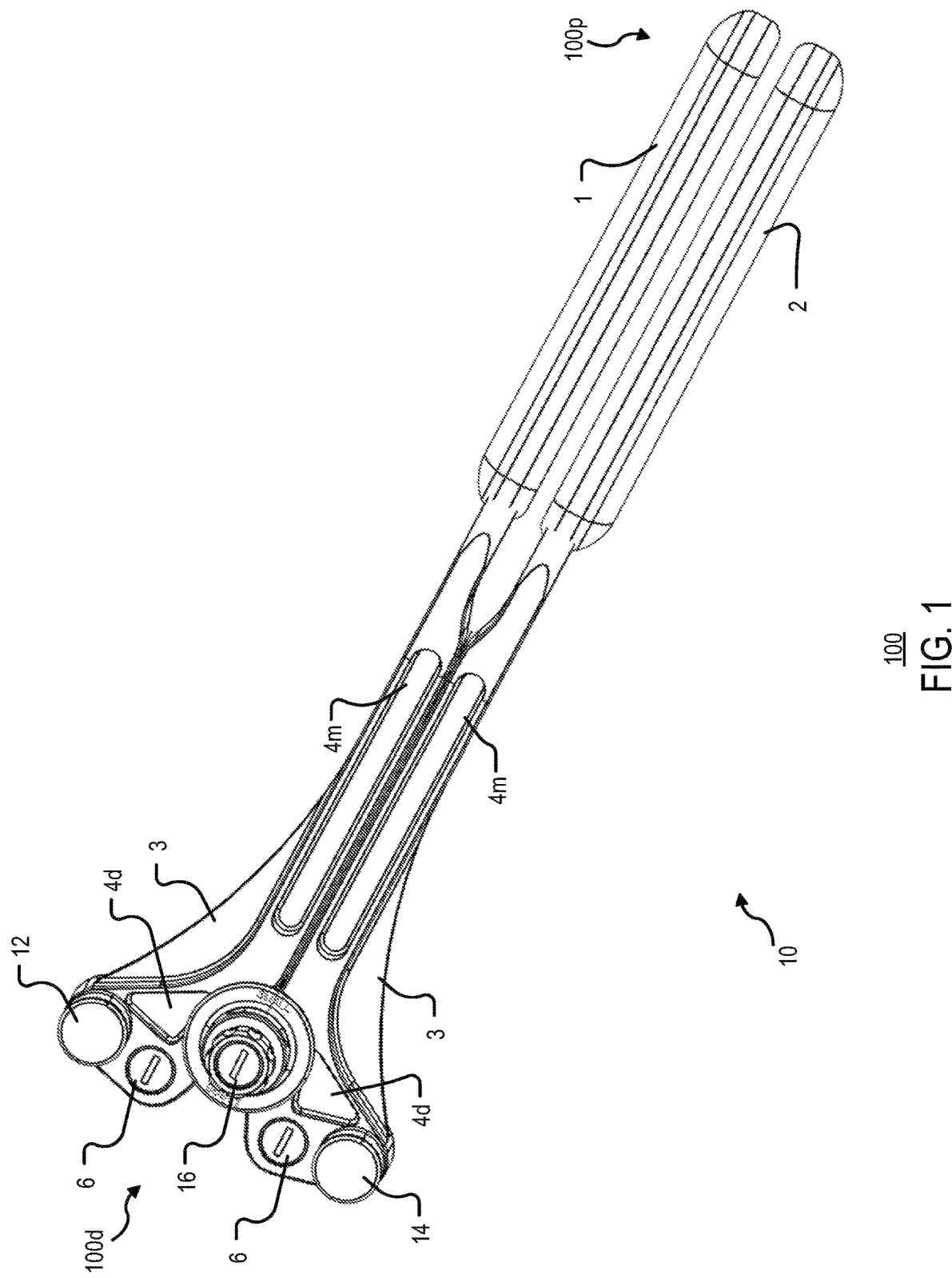
FIG. 1 is a perspective view of a first side of an example rod bender.

Embodiments of the present disclosure relate generally, for example, to spinal stabilization systems, and more particularly, to surgical instruments for use with spinal stabilization systems. Embodiments of the devices and methods are described below with reference to the Figures.

The following discussion omits or only briefly describes certain components, features and functionality related to spinal stabilization systems, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context clearly indicates otherwise.

Terms such as "same," "equal," "planar," "coplanar," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise.

Figure 2:
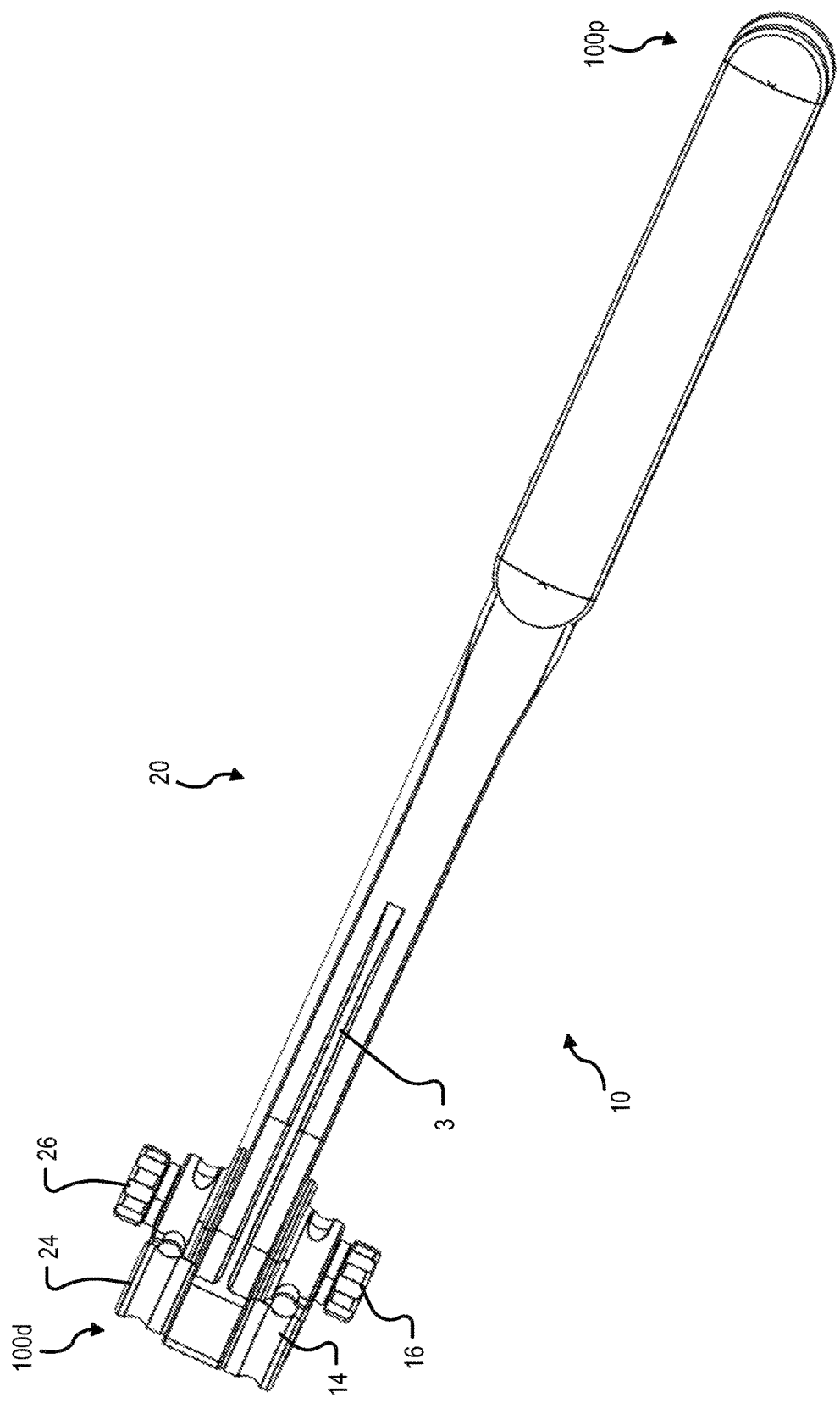
FIG. 2 is a side perspective of the example rod bender.
Figure 3:
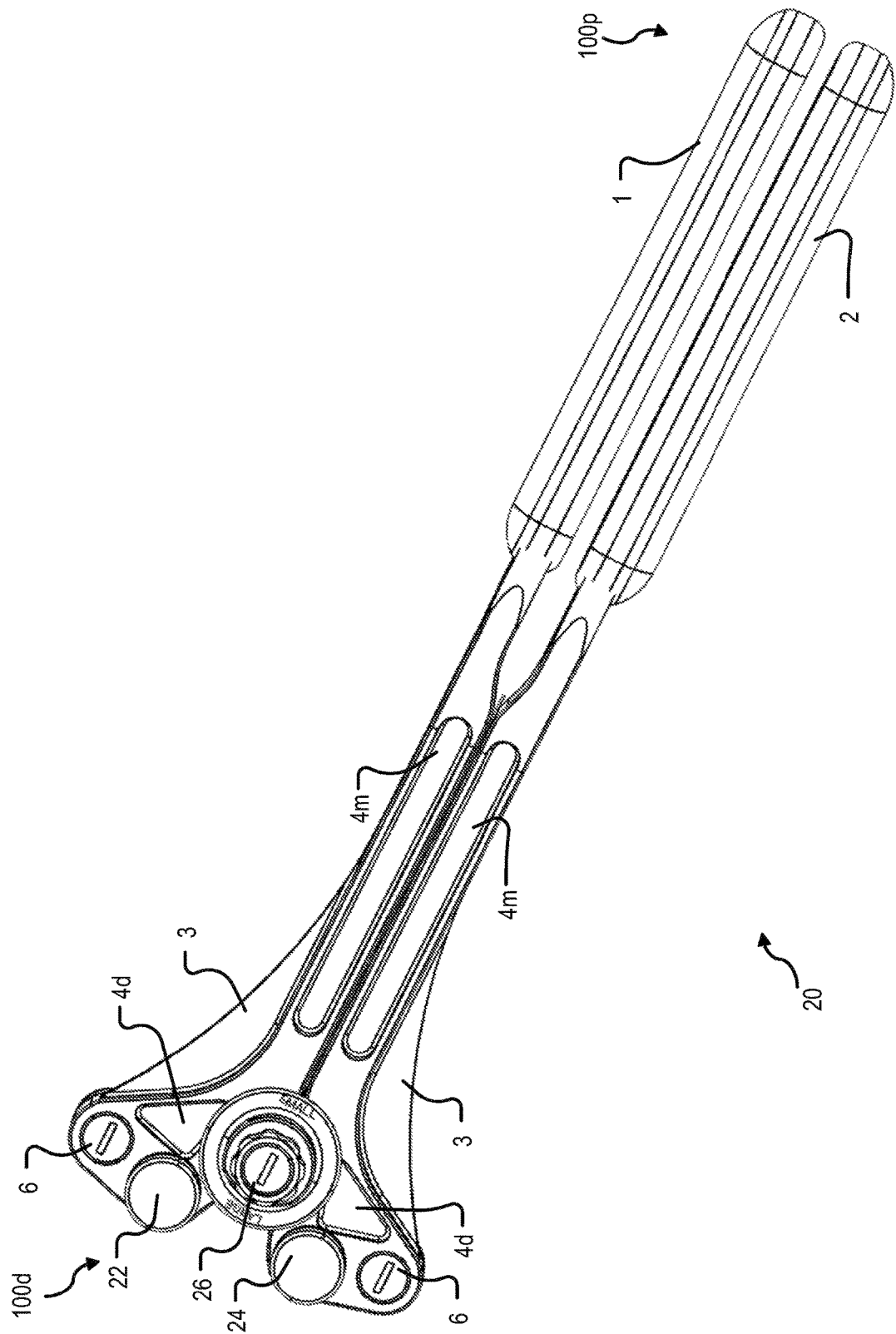
FIG. 3 is a perspective view of a second side of an example rod bender.
Figure 4:
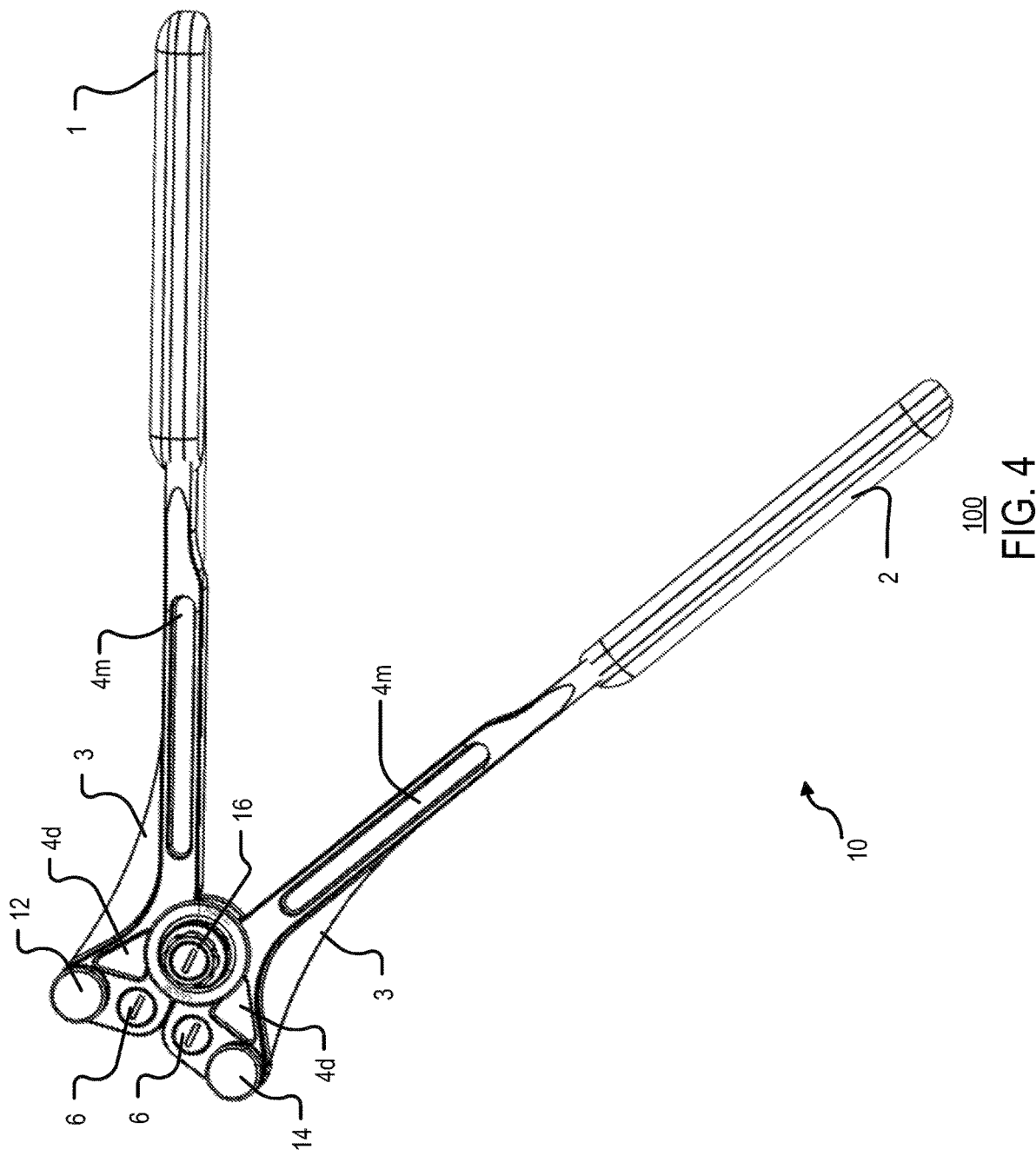
FIG. 4 is a perspective view of a first side of an example rod bender in an open position.
Figure 5:
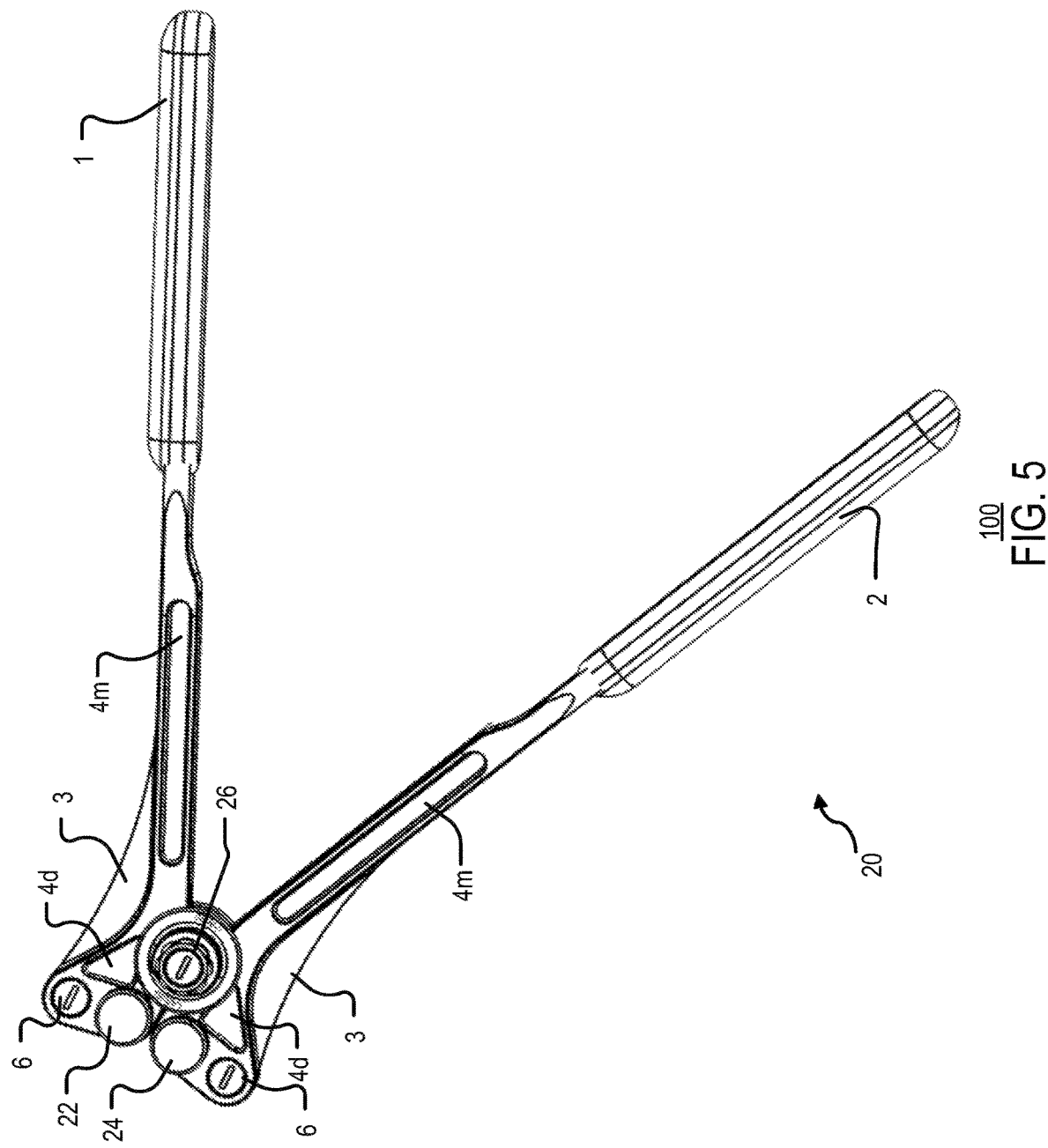
FIG. 5 is a perspective view of a second side of an example rod bender in an open position.
Figure 9:
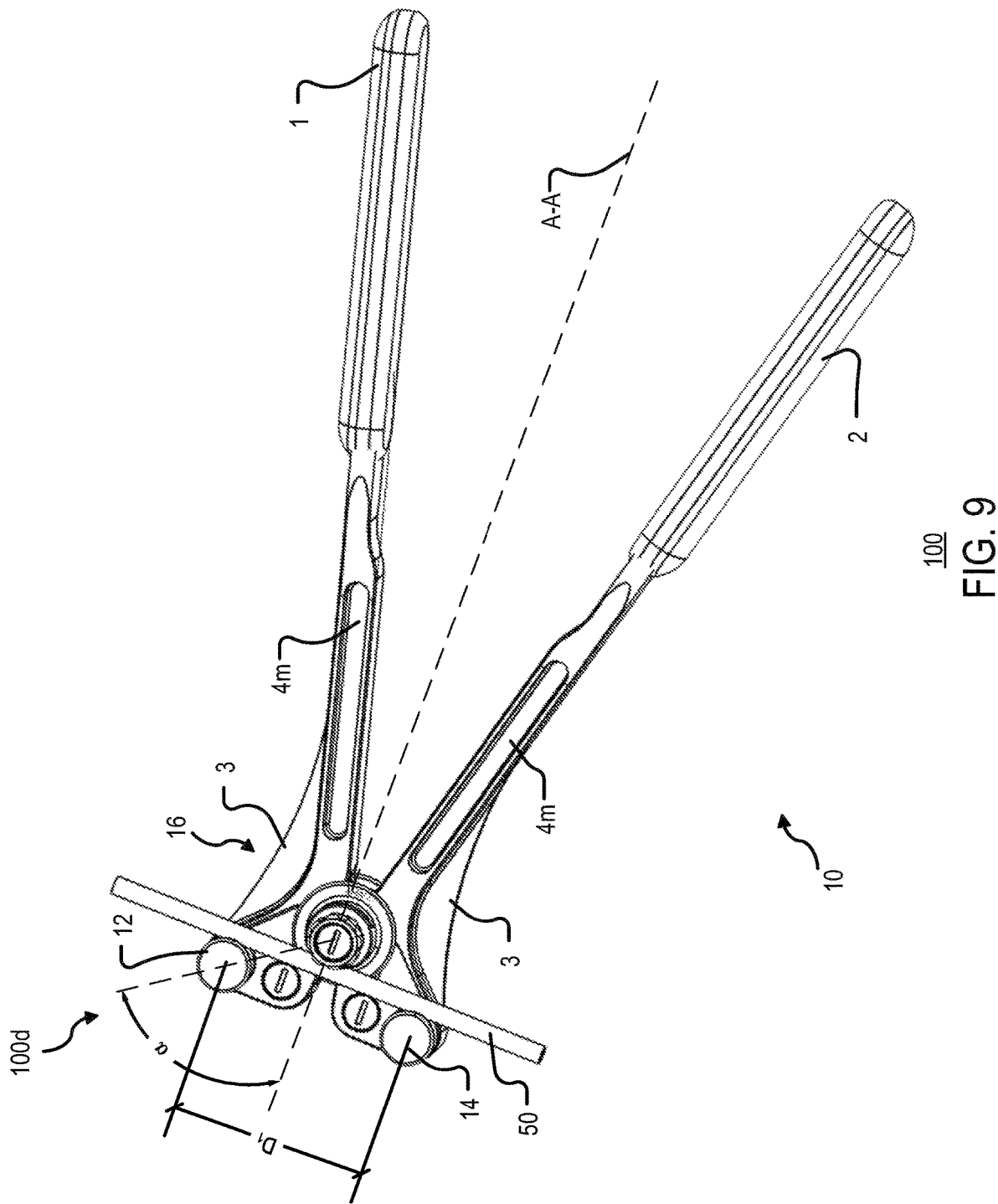
FIG. 9 is a perspective view of a first side of an example rod bender in an open position with a rod before bending the rod.
Figure 10:
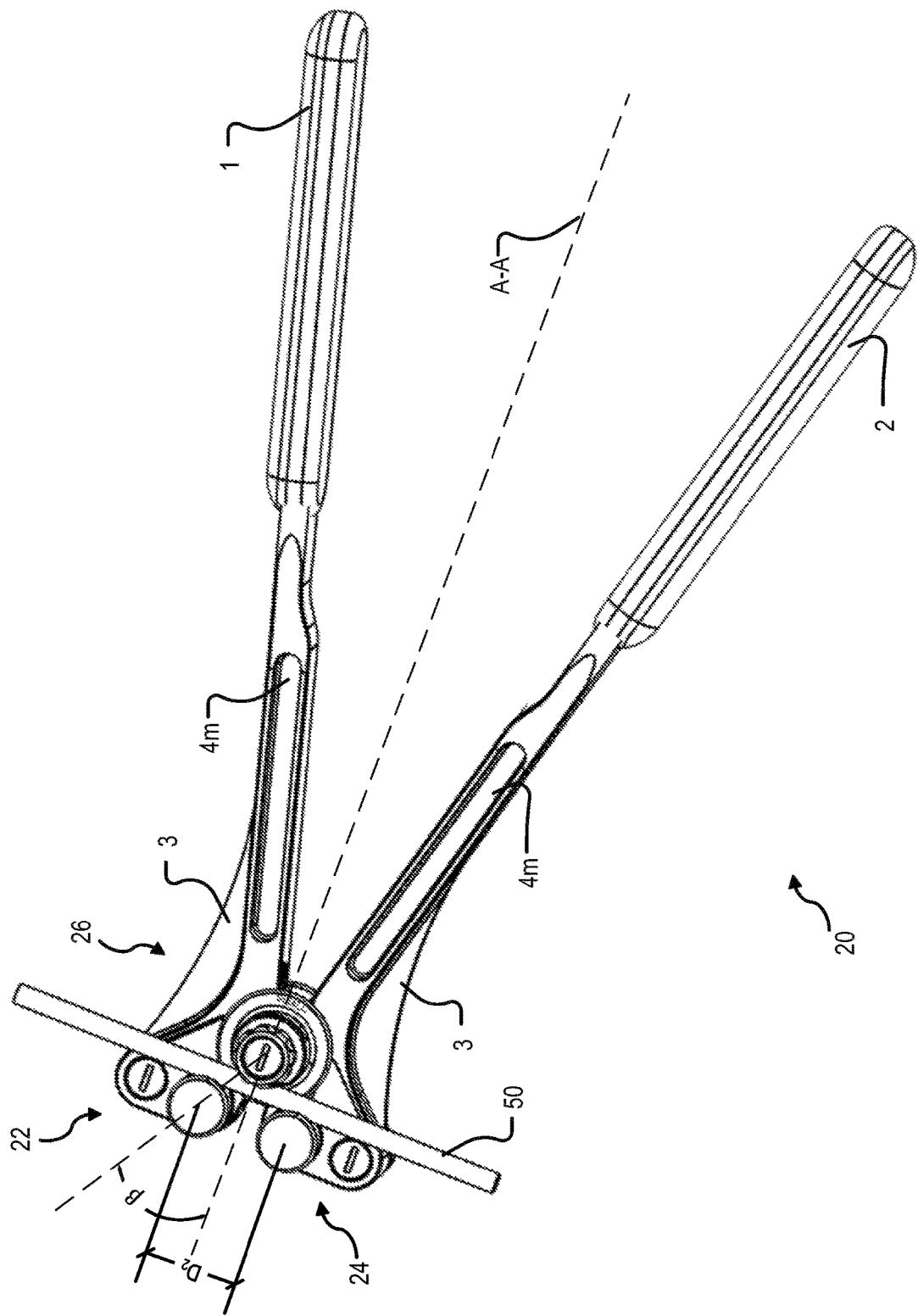
FIG. 10 is a perspective view of a second side of an example rod bender in an open position with a rod before bending the rod.
Figure 11:
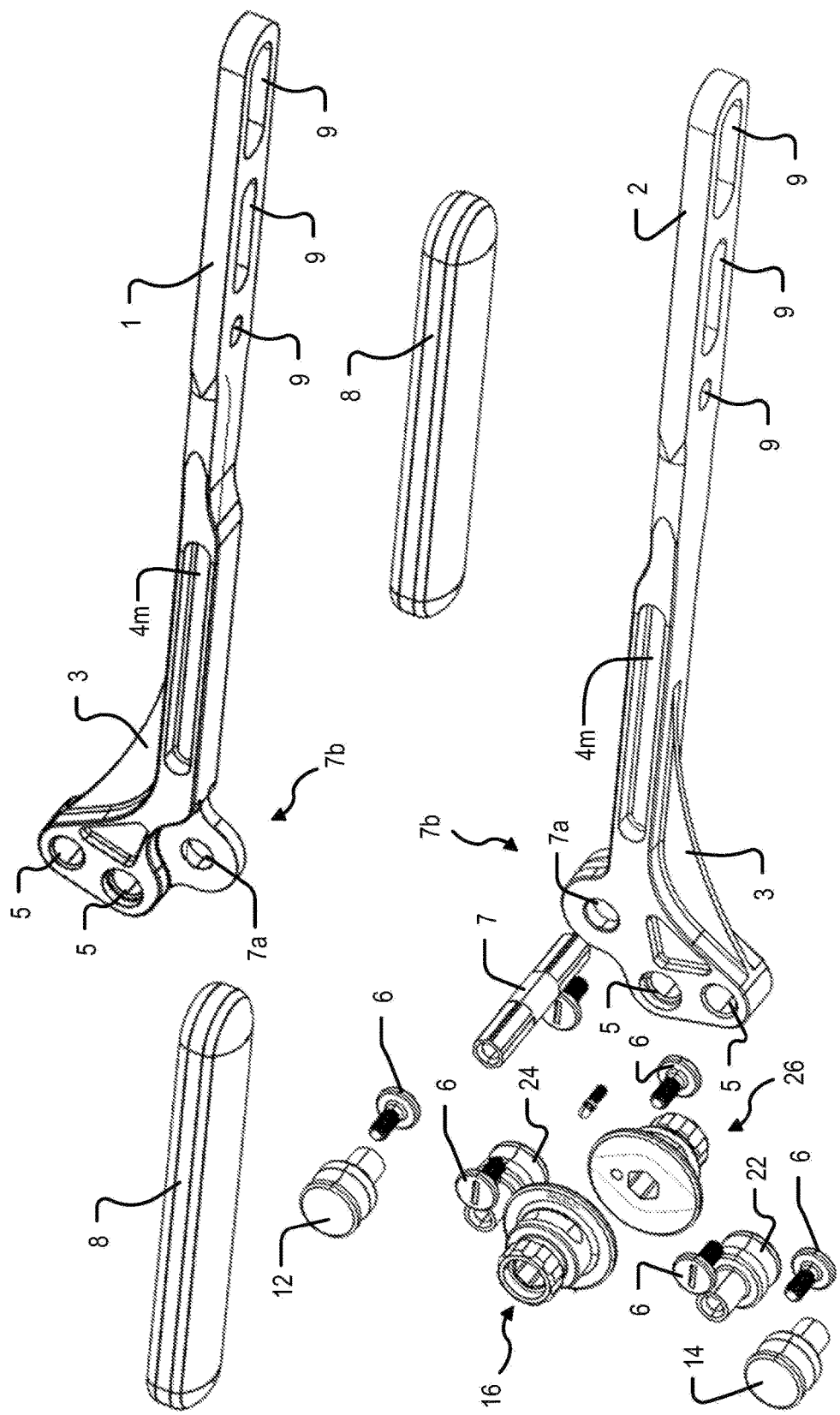
FIG. 11 is an exploded parts diagram of an example rod bender.

Referring generally to FIGS. 1-11 an example rod bender 100 is disclosed. FIG. 1 is a perspective view of a first side 10 of an example rod bender 100, FIG. 2 is a side perspective of rod bender 100, and FIG. 3 is a perspective view of a second side 20 of rod bender 100. FIG. 4 is a perspective view of a first side 10 of an example rod bender 100 in an open position and FIG. 5 is a perspective view of a second side 20 of an example rod bender 100 in an open position. In the illustrated embodiment, rod bender 100 may be a considered a dual-sided rod bender because the first side 10 and the second side 20 are each configured to bend a rod 50, for example. Rod bender 100 may have a proximal end 100p and a distal end 100d. Proximal end 100p may include a first handle 1 and a second handle 2 opposite the first handle 1, for example. Distal end 100d may be configured for seating and bending a rod 50 at first side 10 and/or second side 20, as will be described in further detail below. First handle 1 and second handle 2 may be operably coupled together, i.e., pivotably connected together and rotatable about a pivot. The pivot can be formed by any way known in the art. For example, as illustrated in FIG. 11, a tab 7b may be formed on the first handle 1 and two tabs 7b may be formed on the second handle 2. The tab 7b of the second handle 2 may be seated within a void space between the two tabs 7b of the second handle 2. Additionally, each tab 7b may include a pin aperture 7a through which a pin 7 may pass through and connect the tabs 7b of the first handle 1 and second handle 2 together, for example. In the illustrated embodiment, the first handle 1 and the second handle 2 are pivotably coupled to one another about the pin 7.

First side 10 may have a first roller 12 and a second roller 14. Each of first roller 12 and second roller 14 may be disposed on distal end 100d at opposite lateral ends, for example. Additionally, first roller 12 may include an arcuate channel 12a extending circumferentially along a side surface, for example. Similarly, second roller 14 may include an arcuate channel 14a extending circumferentially along a side surface. The arcuate channels may correspond in size and shape to the cross sectional diameter of a cylindrical rod 50 and be configured for seating the cylindrical shaped rod 50, for example. First side 10 may include a third roller 16 disposed between first roller 12 and second roller 14, for example. In various embodiments, third roller 16 may be disposed above and/or be in a coaxial alignment with pivoting pin 7 (see FIG. 11). Third roller 16 may function as a fulcrum point for bending rod 50, while first roller 12 and second roller 14 apply force on opposite ends of rod 50, for example.

Second side 20 may have a fourth roller 22 and a fifth roller 24. Each of fourth roller 22 and fifth roller 24 may be disposed on distal end 100d at opposite lateral ends, for example. Additionally, fourth roller 22 may include an arcuate channel 22a extending circumferentially along a side surface, for example. Similarly, fifth roller 24 may include an arcuate channel 24a extending circumferentially along a side surface. The arcuate channels may correspond in size and shape to the cross sectional diameter of a cylindrical rod 50 and be configured for seating the cylindrical shaped rod 50, for example. In various embodiments, sixth roller 26 may be disposed above and/or be in a coaxial alignment with pivoting pin 7 (see FIG. 11). Sixth roller 26 may function as a fulcrum point for bending rod 50, while fourth roller 22 and fifth roller 24 apply force on opposite ends of rod 50, for example. Additionally, sixth roller 26 and third roller 16 may be coaxially aligned with pin 7 and connected to pin 7 on opposite sides of rod bender 100.

Each of first handle 1 and second handle 2 may include a support webbing 3. Support webbing 3 may be disposed on a lateral side surface of each respective handle 1 and 2 towards distal end 100d, for example. Additionally, the first side 10 of each of first handle 1 and second handle 2 may have a medial recess 4m disposed medially with respect to proximal end 100p and distal end 100d. Similarly, the first side 10 of each of first handle 1 and second handle 2 may have a distal recess 4d disposed at, adjacent to, and/or proximate to distal end 100d. Likewise, The second side 20 of each of first handle 1 and second handle 2 may have a medial recess 4m disposed medially with respect to proximal end 100p and distal end 100d. Furthermore, the second side 20 of each of first handle 1 and second handle 2 may have a distal recess 4d disposed at, adjacent to, and/or proximate to distal end 100d. At least one advantage of support webbing 3 is the structural reinforcement of rod bender 100 at the distal end 100d Similarly, medial recess 4m and distal recess 4d structurally reinforce handles 1 and 2, for example. In this way, these structural reinforcements provide a strengthened rigid structure that also allows for the reduction of total overall weight of the rod bender 100. For example, due to the structural reinforcements as explained above, the rod bender 100 is sufficiently strong to bend hardened rods 50 such as cobalt chromium (CoCr) rods and the like. Additionally, the structural reinforcements significantly reduce the overall weight of rod bender 100 relative to an alternate surgical tool (not illustrated) not featuring these structural reinforcements.

Figure 6:
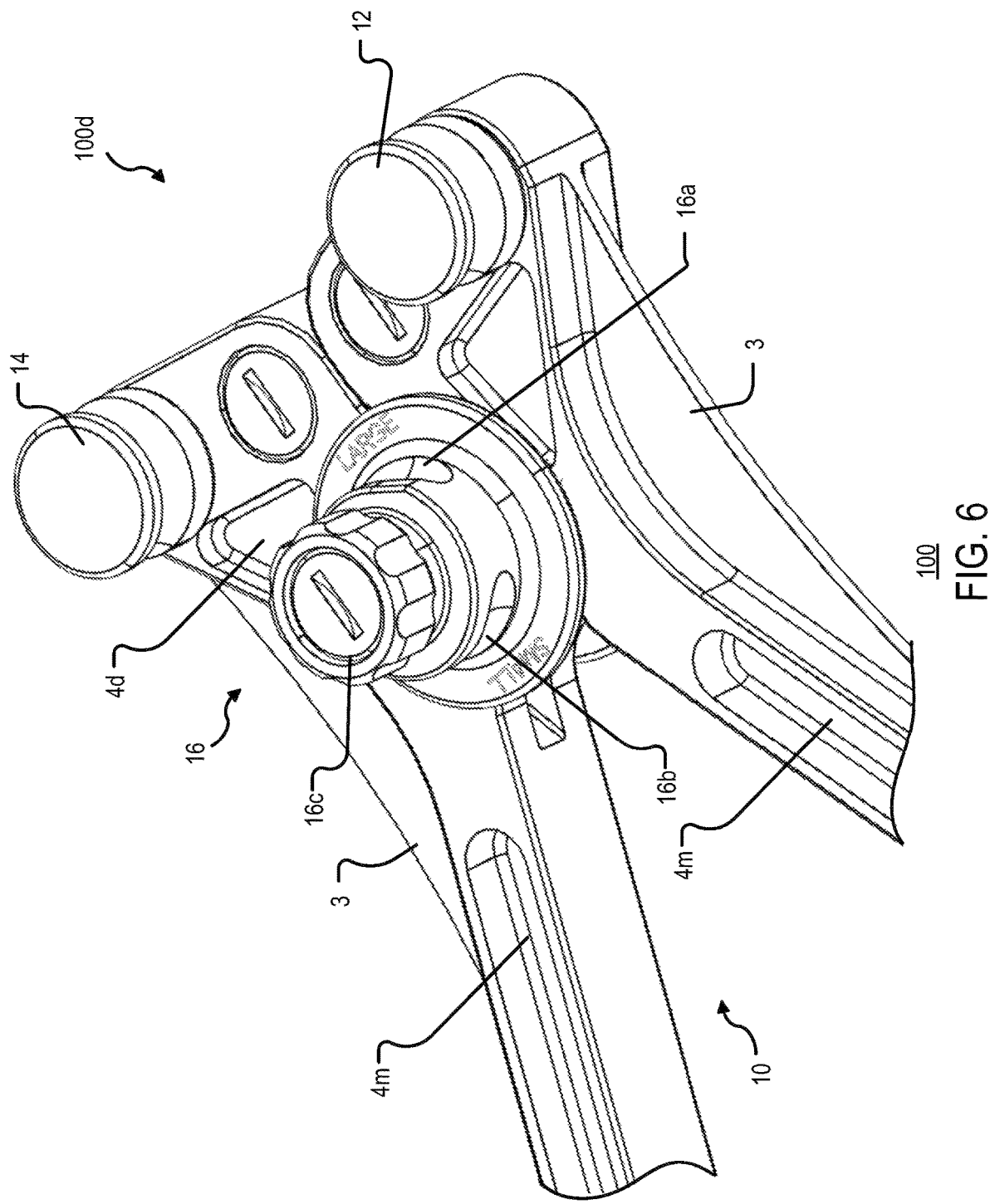
FIG. 6 is an enlarged perspective view of the distal end of a first side of an example rod bender.
Figure 7:
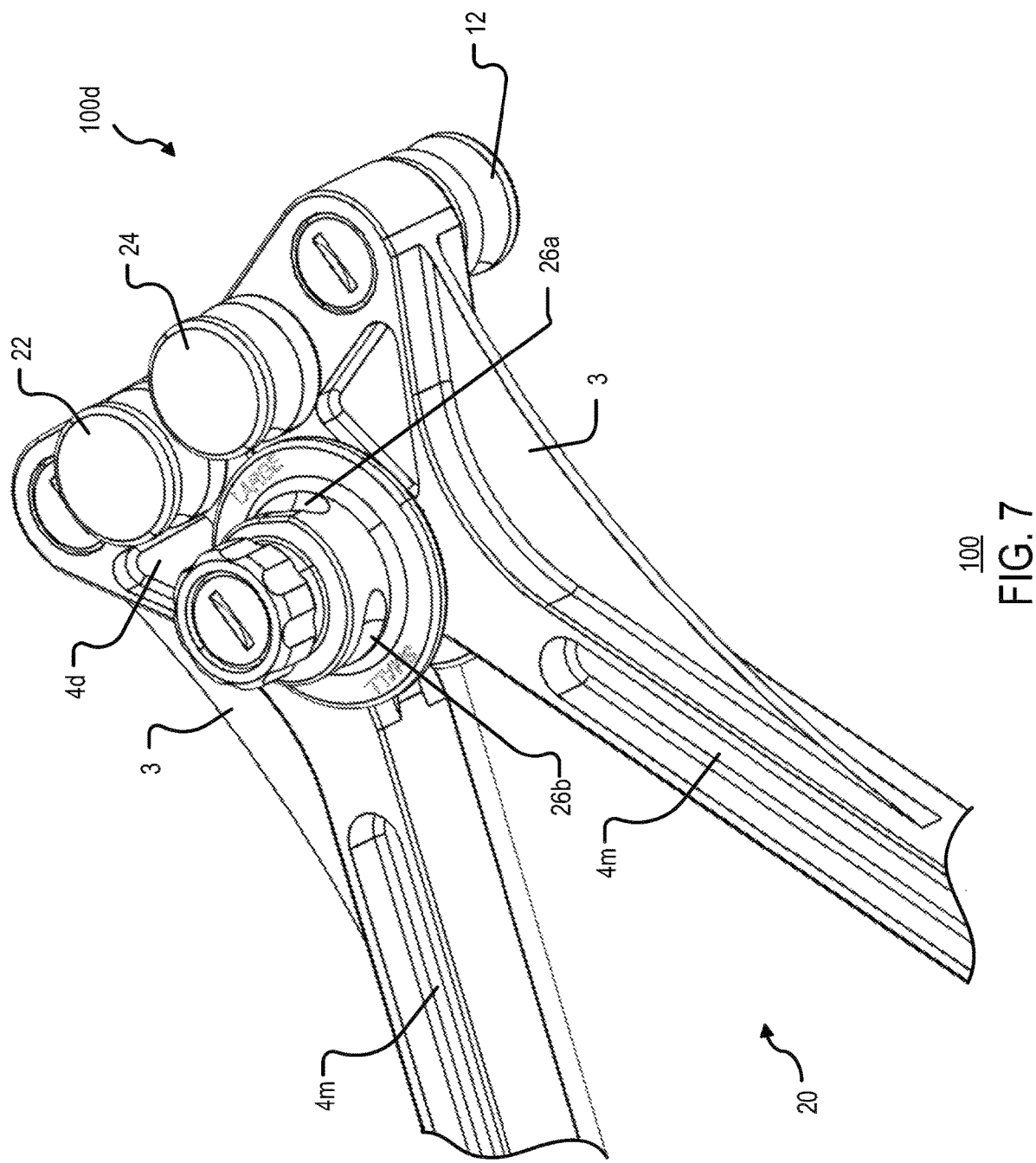
FIG. 7 is an enlarged perspective view of the distal end of a second side of an example rod bender.
Figure 8:
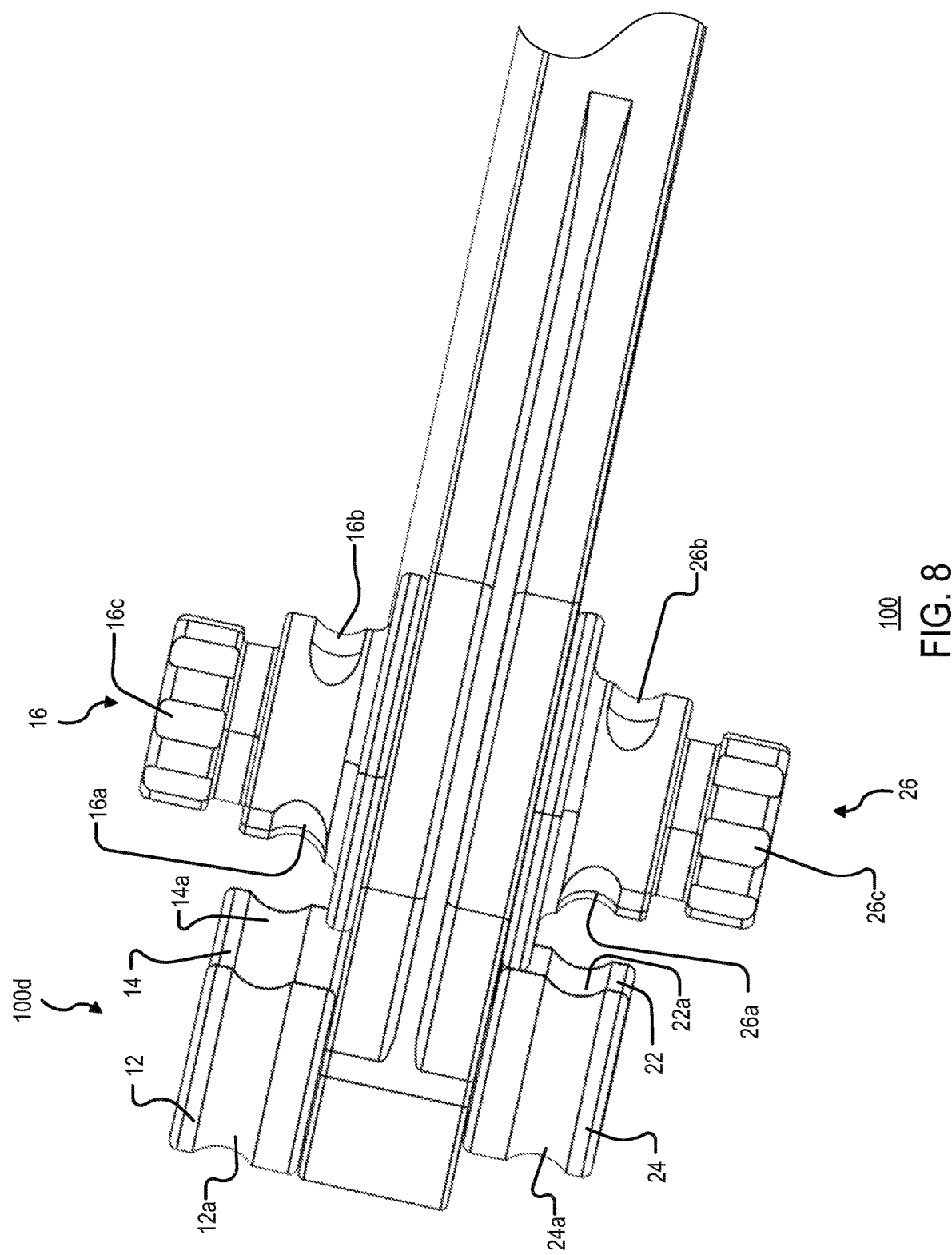
FIG. 8 is an enlarged side perspective view of the distal end of an example rod bender.

FIG. 6 is an enlarged perspective view of the distal end 100d of a first side 10 of an example rod bender 100 and FIG. 7 is an enlarged perspective view of the distal end 100d of a second side 20 of an example rod bender 100. In the example embodiment, it is shown how the support webbing 3 structurally reinforces the rod bender 100 in a similar way to an I-Beam, for example. With reference to FIG. 6, it is shown that third roller 16 includes several additional features. For example, in various embodiments, third roller 16 may be an adjustable roller including a plurality of nesting channels 16a and 16b and a turn dial 16c to switch between nesting channels 16a and 16b. In the example embodiment, a first nesting channel 16a and a second nesting channel 16b are illustrated although other embodiments may have more or less nesting channels 16a and 16b. For example, two, three, or four differently sized nesting channels. Nesting channels 16a and 16b may be configured to seat a rod 50 of different cross sectional diameters, for example. Nesting channels 16a and 16b may be configured to apply different bend radii, for example. In the example embodiment, each nesting channel 16a and 16b is shaped like an arcuate channel extending circumferentially around a portion of a bearing surface of third roller 16. For example, nesting channel 16a extends circumferentially around about 20% to about 40% of a rod bearing surface of third roller 16. Similarly, nesting channel 16b extends circumferentially around about 20% to about 40% of a rod bearing surface of third roller 16. With reference to FIG. 8, nesting channel 16a may seat a rod 50 having a relatively larger cross sectional diameter and nesting cavity 16b may seat a rod 50 having a relatively smaller cross sectional diameter, for example.

With reference to FIG. 7, it is shown that sixth roller 26 includes several additional features. For example, in various embodiments, sixth roller 26 may be an adjustable roller including a plurality of nesting channels 26a and 26b and a turn dial 26c to switch between nesting channels 26a and 26b. In the example embodiment, a first nesting channel 26a and a second nesting channel 26b are illustrated although other embodiments may have more or less nesting channels 26a and 26b. For example, two, three, or four differently sized nesting channels. Nesting channels 26a and 26b may be configured to seat a rod 50 of different cross sectional diameters, for example. Nesting channels 26a and 26b may be configured to apply different bend radii, for example. In the example embodiment, each nesting channel 26a and 26b is shaped like an arcuate channel extending circumferentially around a portion of bearing surface of sixth roller 26. For example, nesting channel 26a extends circumferentially around about 20% to about 40% of a rod bearing surface of sixth roller 26. Similarly, nesting channel 26b extends circumferentially around about 20% to about 40% of a rod bearing surface of sixth roller 26. Nesting channels 26a and 26b may be configured to seat a rod 50 of different cross sectional diameters, for example. With reference to FIG. 8, nesting channel 26a may seat a rod 50 having a relatively larger cross sectional diameter and nesting channel 26b may seat a rod 50 having a relatively smaller cross sectional diameter, for example.

FIG. 9 is a perspective view of a first side 10 of an example rod bender 100 in an open position with a rod 50 before bending the rod 50 and FIG. 10 is a perspective view of a second side 20 of an example rod bender 100 in an open position with a rod 50 before bending the rod 50. In practice, a surgeon may grasp first handle 1 and second handle 2 and spread them apart from one another thereby causing first handle 1 and second handle 2 to pivot about pin 7 and move into an open position, for example. It should be understood that both sides 10 and 20 are each in an open position and either side 10 and/or 20 may receive a rod 50.

In various embodiments, first side 10 may be configured for bending a relatively longer rod 50 and may be useful for apical bends. For example, an outermost edge of roller 12 may be disposed on, adjacent to, and/or immediately proximate to an outermost lateral edge of the distal end 100d of handle 1. Similarly, an outermost edge of roller 14 may be disposed on, adjacent to, and/or immediately proximate to an outermost lateral edge of the distal end 100d of handle 2. For example still, rollers 14 and 12 are disposed on the farthest lateral edges of distal end 100d, respectively, on opposite handles. This positioning of rollers 12, 14, and 16 may be useful for providing a relatively larger mechanical advantage when bending a rod due to rollers 12 and 14 being positioned relatively far away from roller 16, for example.

In various embodiments, second side 20 may be configured for bending a relatively shorter rod 50 and/or for conforming rod 50 in a tighter bend. For example, an innermost edge of roller 22 may be disposed on, adjacent to, and/or immediately proximate to an innermost lateral edge of the distal end 100d of handle 1. Similarly, an innermost edge of roller 24 may be disposed on, adjacent to, and/or immediately proximate to an innermost lateral edge of the distal end 100d of handle 2. For example still, rollers 24 and 22 are disposed on the innermost lateral edges of distal end 100d, respectively, on opposite handles. In various embodiments, the positioning of rollers 22, 24, and 26 may providing a relatively smaller mechanical advantage when bending a rod due to rollers 22 and 24 being positioned relatively close to roller 16, for example.

In the example embodiment, a distance between a center point of roller 12 and a center point of roller 14 may be a first distance $D_1$ (see FIG. 9) and a distance between a center point of roller 22 and roller 24 may be a second distance $D_2$ (see FIG. 10). In the example embodiment, $D_1$ may be greater than $D_2$. Accordingly, the first side 10 may be configured to provide a relatively large mechanical advantage (a first mechanical advantage) when contouring a rod 50 and the second side 20 may be configured to provide a relatively smaller mechanical advantage (a second mechanical advantage) when contouring a rod 50. In preliminary testing, it was determined that the first side 10 may require about 265 Newtons of clamping force to bend a CoCr rod 50 from the open position to the closed position and the second side 20 may require about 345 Newtons of clamping force to bend a CoCr rod 50 from the open position to the closed position. Additionally, in various embodiments, the first side 10 and the second side 20 may be configured to bend a rod 50 by the same degree or amount, i.e., an angle of a bent portion of a rod 50 may be the same when bent on the first side 10 as when bent on the second side 20 (at least when moved to the fully closed position). Furthermore, in at least embodiments, the first side 10 and the second side 20 may be configured to bend a rod 50 by a different degree or amount, i.e., an angle of a bent portion of a rod 50 may be different when bent on the first side 10 as when bent on the second side 20 (at least when moved to the fully closed position).

An angular relationship α (Alpha) between roller 16 and roller 12 may be the same value as an angular relationship α between roller 16 and roller 14, i.e., a first angular relationship α. For example, the first angular relationship may be conceptualized as an angle measured between a longitudinal plane A-A of rod bender 100 and an imaginary line extending from a center point of roller 16 to a center point of roller 12 (and/or roller 14). Longitudinal plane A-A may be understood as a plane extending from a first point positioned equidistant between handles 1 and 2 at proximate end 100d that bisects pin 7 and extends towards distal end 100d. For example, as illustrated in FIG. 9 longitudinal plane A-A is extending from a proximal end 100p to a distal end 100d into the page. Accordingly, when measured with respect to longitudinal plane A-A, an angle α between a center point of roller 16 and a center point of roller 12 may be the same as an angle α between a center point of roller 16 and a center point of roller 14, for example. Similarly, an angular relationship β (Beta) between roller 26 and roller 22 may be the same value as an angular relationship β between roller 26 and roller 24, i.e., a second angular relationship β. Accordingly, when measured with respect to longitudinal plane A-A, an angle β between a center point of roller 26 and a center point of roller 12 may be the same as an angle β between a center point of roller 16 and a center point of roller 14, for example.

Consistent with the above disclosure, the first distance $D_1$ between rollers 12 and 14 and the first angular relationship α between rollers 12 and 16, and 14 and 16 may be referred to as a first geometry, for example. Similarly, the second distance $D_2$ between rollers 22 and 24 and the second angular relationship β between rollers 22 and 26 and 24 and 26 may be referred to as a second geometry, for example. Those with skill in the art will appreciate that in various disclosed example embodiments the first geometry may be defined by the first, second, and third rollers 12, 14, 16 and the first geometry may be configured to provide a first mechanical advantage for bending a rod 50 due to its particular structural arrangement. Similarly, the second geometry may be defined by the fourth, fifth, and sixth rollers 22, 24, and 26 and may be configured to provide a second mechanical advantage for bending a rod 50 due to its particular structural arrangement. Additionally, in various embodiments, the first mechanical advantage may be greater than the second mechanical advantage.

In the example embodiment, and when rod bender 100 is in a closed configuration, the first angular relationship α may be about 50 degrees to about 80 degrees, about 60 degrees to about 70 degrees, and more particularly about 70 degrees. Additionally, and when rod bender 100 is in a closed configuration, the second angular relationship β may be about 30 degrees to about 60 degrees, about 40 degrees to about 50 degrees, and more particularly about 50 degrees. In at least one embodiment, the first angular relationship is about 70 degrees and the second angular relationship is about 47 degrees. Additionally, a ratio of the first angular relationship to the second angular relationship may be about 1.5 when rod bender 100 is in a closed configuration. In this way, the first angular relationship of the first side 10 and the second angular relationship of the second side 20 are configured for conforming different bends in a rod 50. For example, first side 10 may be utilized to create a larger more gentler bend and/or for a longer rod 50. For example still, second side 20 may be utilized to create a sharper more pronounced bend and/or for a shorter rod 50.

In practice, an end user such as a surgeon may grasp first handle 1 and second handle 2 and spread them apart from one another thereby causing first handle 1 and second handle 2 to pivot about pin 7 and move rod bender 100 into an open position, for example. It should be understood that both sides 10 and 20 are each in an open position and either side 10 and/or 20 may receive a rod 50. Next, the surgeon may insert a rod 50 between rollers 12, 14, and 16 of first side 10, for example. Next, the surgeon may rotate the turn dial 16c to position either one of 16a or 16b such that it faces rod 50. The surgeon may choose which one of 16a or 16b faces rod 50 in view of the cross sectional diameter of rod 50 as previously explained above. It should also be understood that the surgeon may rotate the turn dial 16c in advance of inserting the rod 50 between rollers 12, 14, and 16. Next, and in some embodiments, the surgeon may lock turn dial 16c in a fixed non-rotatable position. Next, the surgeon may gently close handles 1 and 2 such that rod 50 is nested within one of nesting channels 16a or 16b of roller 16 and the arcuate channels 12a and 14a of rollers 12 and 14. Next, the surgeon may grasp handles 1 and 2 and apply a force to each handle bringing the proximate end 100d of each handle closer together. For example, the surgeon may apply a first clamping force closing handles 1 and 2 thereby bending rod 50 due to a first mechanical advantage provided by the first side 10. It should be understood the surgeon may only partially close handles 1 and 2 in some situations where a more modest bend is desired. Optionally, the surgeon may reposition rod 50 and/or continue to contour rod 50 with respect to first side 10 in similar fashion as explained above. Thereafter the surgeon may release handles 1 and 2 and move rod bender 100 away from rod 50 (or vice versa).

Additionally, or alternatively, a surgeon may continue to contour rod 50 and/or contour a second rod 50. For example, the surgeon may place the same rod 50 or a new rod 50 between rollers 22, 24, and 26 of second side 20, for example. Next, the surgeon may rotate turn dial 26c to position either one of 26a or 26b such that it faces rod 50. The surgeon may choose which one of nesting channels 26a or 26b faces rod 50 in view of the cross sectional diameter of rod 50 as previously explained above. It should also be understood that the surgeon may rotate the turn dial 26c in advance of inserting the rod 50 between rollers 12, 14, and 16. Next, and in some embodiments, the surgeon may lock turn dial 26c in a fixed non-rotatable position. Next, the surgeon may gently close handles 1 and 2 such that rod 50 is nested within a one of nesting channels 26a or 26b of roller 26 and the arcuate channels 12a and 14a of rollers 12 and 14. Next, the surgeon may grasp handles 1 and 2 and apply a force to each handle bringing the proximate end 100d of each handle closer together. For example, the surgeon may apply a second clamping force closing handles 1 and 2 thereby bending rod 50 due to a second mechanical advantage provided by the second side 20. It should be understood the surgeon may only partially close handles 1 and 2 in some situations where a more modest bend is desired. Optionally, the surgeon may reposition rod 50 and/or continue to contour rod 50 with respect to second side 20 in similar fashion as explained above. Thereafter the surgeon may release handles 1 and 2 and move rod bender 100 away from rod 50 (or vice versa).

FIG. 11 is an exploded parts diagram of an example rod bender 100. In the example embodiment, each handle 1 and 2 include a plurality of weight reducing slots and apertures 9. The weight reducing slots and apertures 9 may be covered by a grip 8 and/or utilized as a means to secure grip 8 to handles 1 and 2, for example. Rollers 12, 14, 22, and 24, may each have a threaded projection that is configured to extend through a roller aperture 5, for example. Roller aperture 5 may have a size and shape corresponding to a size and shape of the threaded projection. In turn, a retaining screw 6 may be threaded and/or otherwise tightened into the interior space of each threaded projection of each of rollers 12, 14, 22, and 24 thereby fixing rollers 12, 14, 22, and 24 with respect to one of handle 1 or handle 2. Roller 16 and roller 26 may each have an aperture therein configured to couple to opposite ends of pin 7. For example, rollers 16 and 26 each have a hexagonal aperture configured to couple to an end portion of pin 7, for example. In various embodiments, each aperture of each roller 16 and 26 may have a size and shape generally corresponding to a cross sectional shape of end portions of pin 7, for example. Additionally, in various embodiments, a central portion of pin 7 may be smooth surface defined by a cylinder and have a generally circular cross sectional shape, for example. The central portion of pin 7 may facilitate pivoting of handles 1 and 2 about pin 7. Additionally, pin 7 may couple handles 1 and 2 together by extending through the two tabs of handle 2 at the pin aperture 7a and the pin aperture of the tab of handle 1, for example.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

What is claimed is:

1. A dual-sided rod bender for contouring a rod, comprising:
    a first handle and a second handle pivotably coupled together, the first handle and second handle each extending in a longitudinal direction from a proximal end to a distal end, respectively;
    wherein the dual-sided rod bender has a first side comprising:
        a first roller coupled to the first handle adjacent the distal end;
        a second roller coupled to the second handle adjacent the distal end;
        a third roller disposed between the first roller and the second roller;
    wherein the dual-sided rod bender has a second side comprising:
        a fourth roller coupled to the first handle adjacent the distal end;
        a fifth roller coupled to the second handle adjacent the distal end;
        a sixth roller disposed between the fourth roller and the fifth roller;
    wherein a first geometry defined by the first, second, and third rollers is configured to provide a first mechanical advantage for bending a rod and a second geometry defined by the fourth, fifth, and sixth rollers is configured to provide a second mechanical advantage for bending a rod, the first mechanical advantage being greater than the second mechanical advantage;
    wherein the third roller further comprises a first adjustment knob, the first adjustment knob including a first nesting channel having a first width and a second nesting channel having a second width, the first adjustment knob being configured to selectively position either one of the first nesting channel or second nesting channel in a position to nest with a rod; and
    wherein the sixth roller further comprises a second adjustment knob, the second adjustment knob including a third nesting channel having a third width and a fourth nesting channel having a fourth width, the second adjustment knob being configured to selectively position either one of the third nesting channel or fourth nesting channel in a position to nest with a rod.

2. The dual-sided rod bender of claim 1, wherein the third roller of the first side is coaxially aligned with the sixth roller of the second side.

3. The dual-sided rod bender of claim 1, wherein the first handle and second handle are pivotably coupled by a pin.

4. The dual-sided rod bender of claim 3, wherein:
    the first handle comprises a first tab and the second handle comprises a second tab and a third tab;
    the first tab is positioned between the second tab and the third tab; and
    the pin extends through the first, second, and third tabs.

5. The dual-sided rod bender of claim 4, wherein the third roller is coupled to the pin at the first side and the sixth roller is coupled to the pin at the second side.

6. The dual-sided rod bender of claim 1, wherein:
    the first roller is disposed adjacent an outer edge of the distal end of the first handle;
    the second roller is disposed adjacent an outer edge of the distal end of the second handle; and
    the third roller is disposed apart from and proximal of the first roller and the second roller.

7. The dual-sided rod bender of claim 6, wherein:
    the fourth roller is disposed adjacent an inner edge of the distal end of the first handle;
    the fifth roller being disposed adjacent an inner edge of the distal end of the second handle; and
    the sixth roller is disposed apart from and proximal of the first roller and second roller.

8. The dual-sided rod bender of claim 1, wherein:
    the first handle has a first longitudinal recess disposed on a medial portion of the first handle and a first distal recess disposed on the distal end of the first handle; and
    the second handle has a second longitudinal recess disposed on a medial portion of the second handle and a second distal recess disposed on the distal end of the second handle.

9. The dual-sided rod bender of claim 8, wherein the first handle has a first support webbing and the second handle has a second support webbing.

10. The dual-sided rod bender of claim 1, wherein a longitudinal plane bisects the dual-sided rod bender by passing through a center of the third roller and a center of the sixth roller.

11. The dual-sided rod bender of claim 10, wherein a first angle measured from an intersection of the longitudinal plane and the center of the third roller to a center of the first roller is the same as a second angle measured from an intersection of the longitudinal plane and the center of the third roller to a center of the second roller.

12. The dual-sided rod bender of claim 11, wherein a third angle measured from an intersection of the longitudinal plane and the center of the sixth roller to a center of the fourth roller is the same as a fourth angle measured from an intersection of the longitudinal plane and a center of the sixth roller to a center of the fifth roller.

13. The dual-sided rod bender of claim 12, wherein the first angle and the second angle define a first angular relationship and the third angle and the fourth angle define a second angular relationship, the first angular relationship being greater than the second angular relationship.

\* \* \* \* \*